United States Patent [19]
Fisk et al.

[11] Patent Number: 5,413,606
[45] Date of Patent: May 9, 1995

[54] INTRAOPERATIVE METHOD OF RESTORING THE SURFACE SMOOTHNESS OF TOTAL KNEE REPLACEMENT COMPONENTS

[76] Inventors: Albert W. Fisk, 1741 Carl Dr.; Thomas S. Fisk, 3077 Winchester Dr., both of Rescue, Calif. 95672

[21] Appl. No.: 103,148

[22] Filed: Aug. 9, 1993

[51] Int. Cl.$^6$ .................... A61F 2/38; A61F 2/30
[52] U.S. Cl. ............................. 623/20; 623/18
[58] Field of Search .............. 623/20, 23, 22, 18

[56] References Cited

PUBLICATIONS

Convention Highlights, American Academy of Orthopaedic Surgeons 60th Annual Meeting, vol. 12: Feb. 1993, Published by Academy Professional Information Services, Inc., San Francisco, Calif. "Laser and SEM-Polished Femoral Components 'Like New'" pp. 7 and 8.

Primary Examiner—David H. Willse
Attorney, Agent, or Firm—Lothrop & West

[57] ABSTRACT

An intraoperative method is provided for the restoration of the bearing surface smoothness of an otherwise well-fixed and well-aligned femoral knee component. This method is an alternative, in appropriate circumstances, to total component replacement. Polishing and buffing techniques are disclosed which substantially reduce the depth and areal extent of scratches and abrasions resulting from metal to metal contact, particularly between a worn, metal-backed patellar component and a femoral component, as well as abrasions resulting from migration of debris that imbeds itself in plastic bearing surfaces prior to surgical reintervention, primarily in the distal condyle areas. Debris generated by the polishing process, along with saline solution, or the like, washes used to flush the debris are isolated from the surgical field by a specially designed draping system.

7 Claims, 3 Drawing Sheets

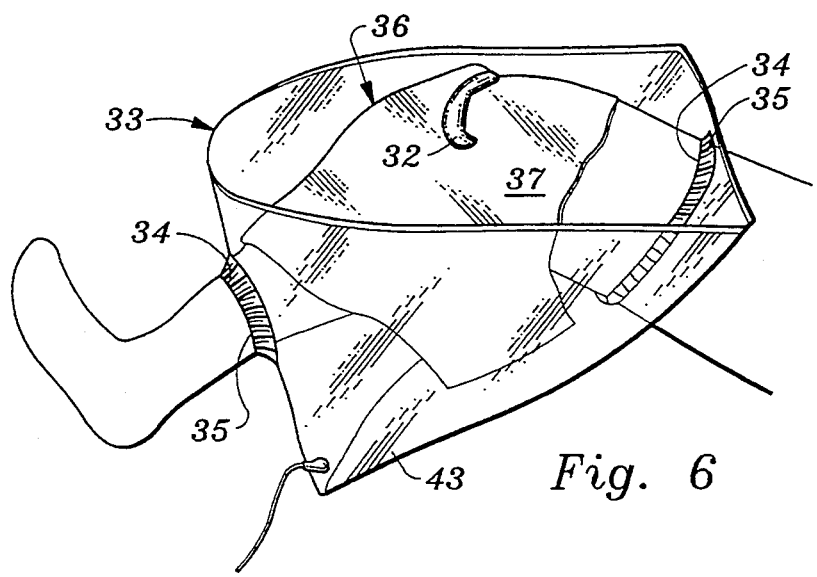
Fig. 6
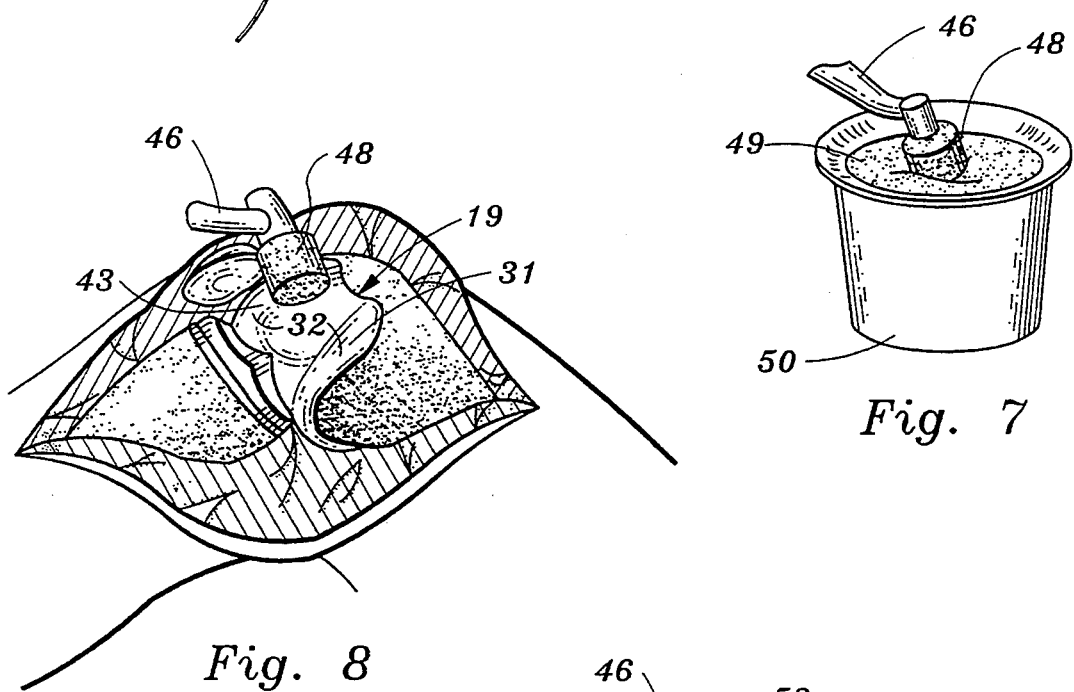
Fig. 8
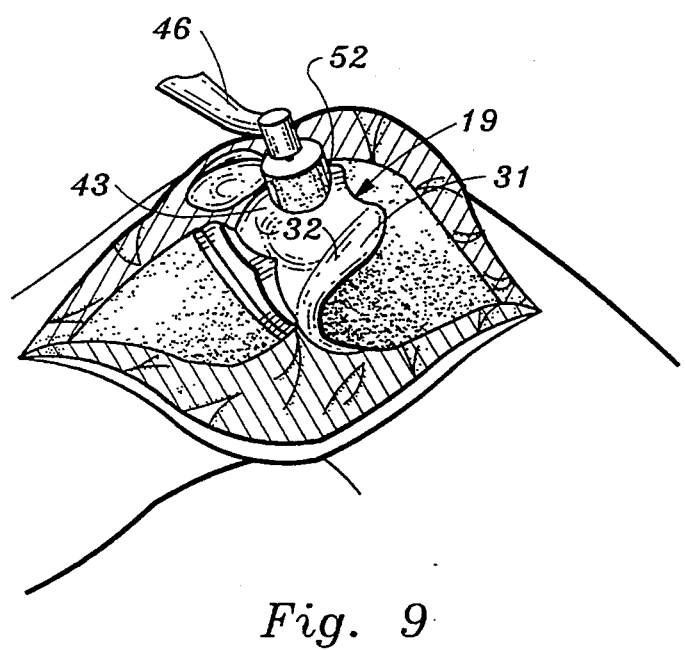
Fig. 7
Fig. 9

INTRAOPERATIVE METHOD OF RESTORING THE SURFACE SMOOTHNESS OF TOTAL KNEE REPLACEMENT COMPONENTS

BACKGROUND OF THE INVENTION

The invention relates generally to arthroplastic implants and, more specifically, to the restoration of total knee replacement (TKR) components as an alternative to total knee revision.

Osteoarthritis is defined as a noninflammatory degenerative joint disease occurring chiefly in older persons. Often, as a consequence of joint deterioration, it becomes advisable or necessary to replace the joint, such as hip, shoulder or knee, for example, with an artificial one. The surgical procedure involved is termed arthroplasty and is widely known and used.

Where the knee is the joint involved, the procedure entails the implantation of prosthetic components designed to reproduce the anatomic movement of the knee and the procedure is termed total knee replacement (TKR).

The artificial implants, or prosthetic components in a total knee replacement are ordinarily constructed of a metal alloy, with some components also incorporating a layer of plastic material to provide a smooth articulating surface.

The metal joint components are very strong, being secured to the bone by fixation studs and special adhesives, and are resistant to surface abrasion and scratching except where metal to metal contact occurs.

The plastic components used in conjunction with the metal components do not wear as well as the metal. Owing to this fact, the plastic material often wears through and metal to metal surfaces come into contact, with resultant scratching or abrasion of the metal components.

This problem especially seems to arise with the patellar component, a button-shaped element which can be made of plastic material but with a metal backing. As the knee is flexed, the metal femoral component can eventually wear away the adjacent plastic layer of the artificial patella and come into contact with the metal backing of the patella. Continued metal to metal contact, as the knee is flexed, results in abrasion and scratching. The surface roughness of the two face to face metal components continues to worsen and eventually results in an intolerable level of discomfort for the wearer. Surface scratching and abrasion of the components can also significantly reduce the strength and fatigue resistance of the implant system as a whole.

Heretofore, it has generally been necessary, even in the case of an otherwise well-fixed and well-aligned total knee femoral component, to remove and replace the rigidly implanted metal prosthesis. Revision of one or more total knee replacement components, particularly the femoral component, is a traumatic procedure and the weakened support structure resulting from bone loss which frequently occurs during total revision arthroplasty makes such procedure undesirable.

Until now, however, there were no other options.

For further background, reference is made to an article entitled "Laser and SEM-Polished Femoral Components: 'Like New'" which appeared on pages seven and eight of CONVENTION HIGHLIGHTS, American Academy of Orthopaedic Surgeons 60th Annual Meeting, Volume 12: February 1993, Published by Academy Professional Information Services, Inc., San Francisco, Calif., a copy of which is provided in the Information Disclosure Statement filed with the present application. It is to be noted that at the end of the article, the name Tom Fisk, BS, appears. This Tom Fisk is one of the co-inventors in the present application.

SUMMARY OF THE INVENTION

The present invention relates to an intraoperative technique, applicable to joints including hip and shoulder but especially to a procedure involving total knee replacement (TKR) components, which provides the surgeon with an option to leave an abraded and scratched component in place in order to avoid the damage that revision surgery may occasion, especially where femoral bone stock loss is involved.

The present method is based upon the use of certain polishing and buffing techniques which enable the surgeon to restore the abraded and scratched surfaces to the substantially mirror finish characteristic of new implants, once a surgical judgment has been made to retain the well-fixed and well-aligned implant.

An important aspect of the method involves the utilization of special drapes, or dams to isolate the surgical field from the debris generated by the polishing steps.

BRIEF DESCRIPTION OF THE DRAWING FIGURES

Figure 3:
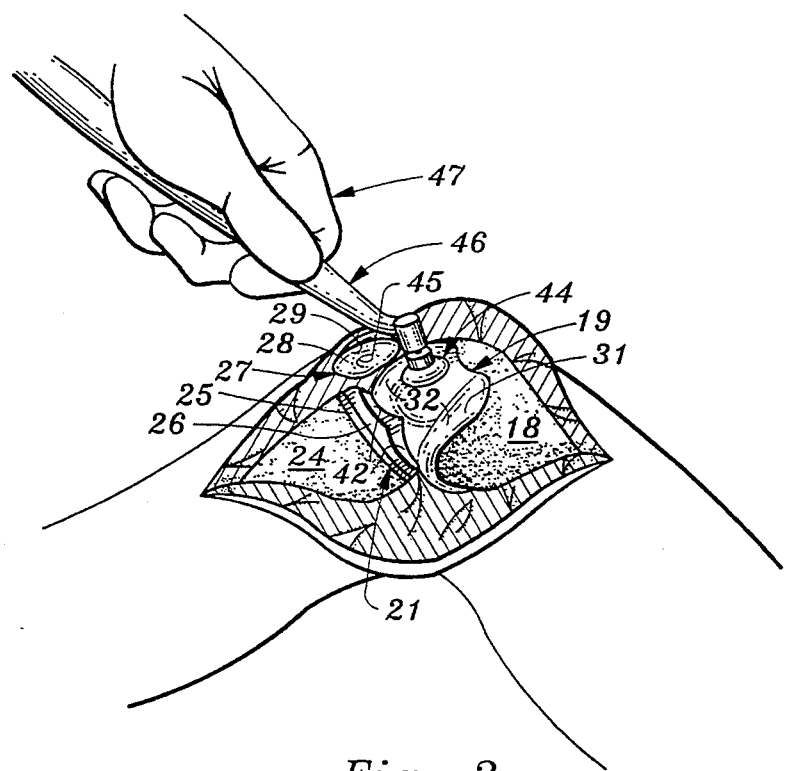
FIG. 3 is a perspective view with the abraded and scratched knee components surgically exposed and showing a relatively high speed flexible abrasive polishing wheel being manipulated so as to remove the most prominent abrasions on the bearing surfaces of the femoral component, the primary and secondary surgical drapes, or dams not being shown in order to clarify the disclosure.

FIG. 6 is a fragmentary perspective view, to a reduced scale, showing the primary dam, or drape, installed in constricting position around the base of a condyle of the femoral component and the fenestrated secondary dam, or drape, with the patient's leg positioned through the elastic windows, a portion of the primary dam being broken away to show the elastic band around the perimeter of the thigh window in the secondary drape;

FIG. 7 is a fragmentary perspective view to an enlarged scale showing a typical felt metal finishing bob buffing wheel pressed against a solid state sterile polishing compound within a container, the heat of friction being sufficient to melt the compound, allowing the sterile compound to adhere to and impregnate the felt bob;

FIG. 8 is a fragmentary perspective view similar to FIG. 3 but illustrating one typical orientation of a cylindrical felt bob in blending and feather edging the bearing surface to be smoothed; and, FIG. 9 is a view similar to FIG. 7 but showing an oval felt bob used in contouring the surface of the smoothed area.

DETAILED DESCRIPTION OF THE INVENTION

Although the intraoperative method of the present invention is susceptible of several variations, it has especially been utilized as taught herein to restore abraded and scratched femoral components to a level comparable to new implants thereby avoiding the need for total revision arthroplasty.

The average hospital stay for a patient following a total revision arthroplasty is eight days. The average stay for patients following the present component-smoothing procedure is four days.

Other advantages include reduction in duration of surgery, reduction in bone loss, and reduction in compromised joint fixation and possible ligament damage as well as diminished risk of infection and mechanical complications.

Although it is believed that the technique disclosed herein is also capable of use in surgical decisions involving arthroplasties of hip, shoulder and elbow joints, the present procedure is especially concerned with a specific intraoperative technique to counter wear resulting from a metal-backed patella on the femoral component, as described by Jeffrey K. Taylor, MD, of Sacramento, Calif., in the article "Laser and SEM-Polished Femoral Components: 'Like New'" published February 1993, cited above.

Figure 1:
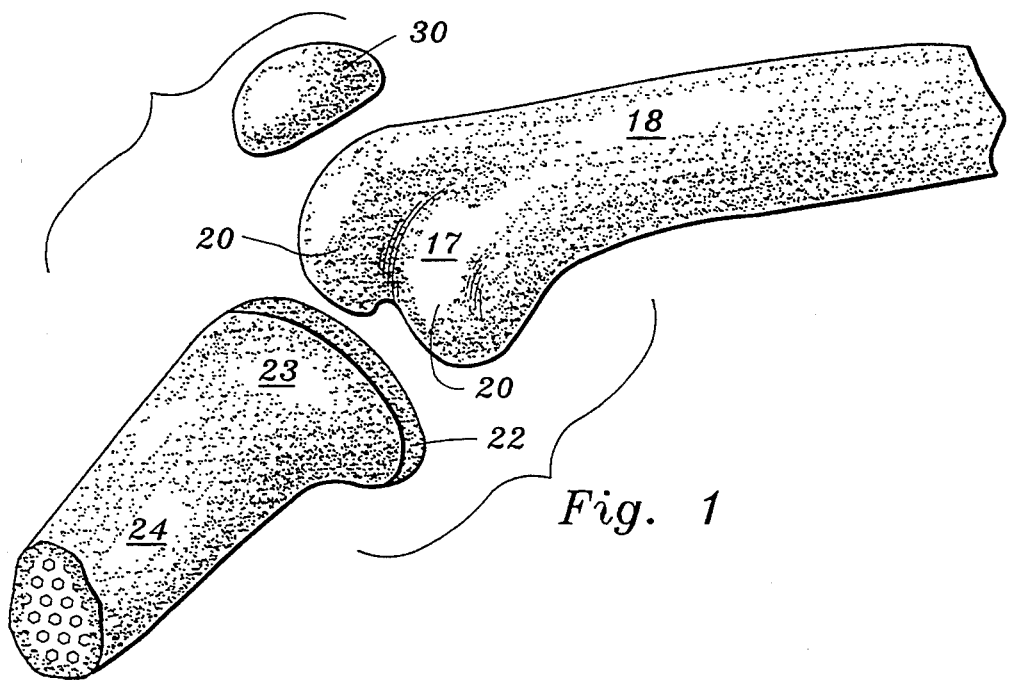
FIG. 1 is a fragmentary, exploded, perspective view, in stylized form, of a partially flexed normal knee joint with the fibula omitted and with the muscles, arteries, tendons, ligaments, and skin not shown in order to clarify the relation between the distal femur, the patella and the proximal tibia.
Figure 2:
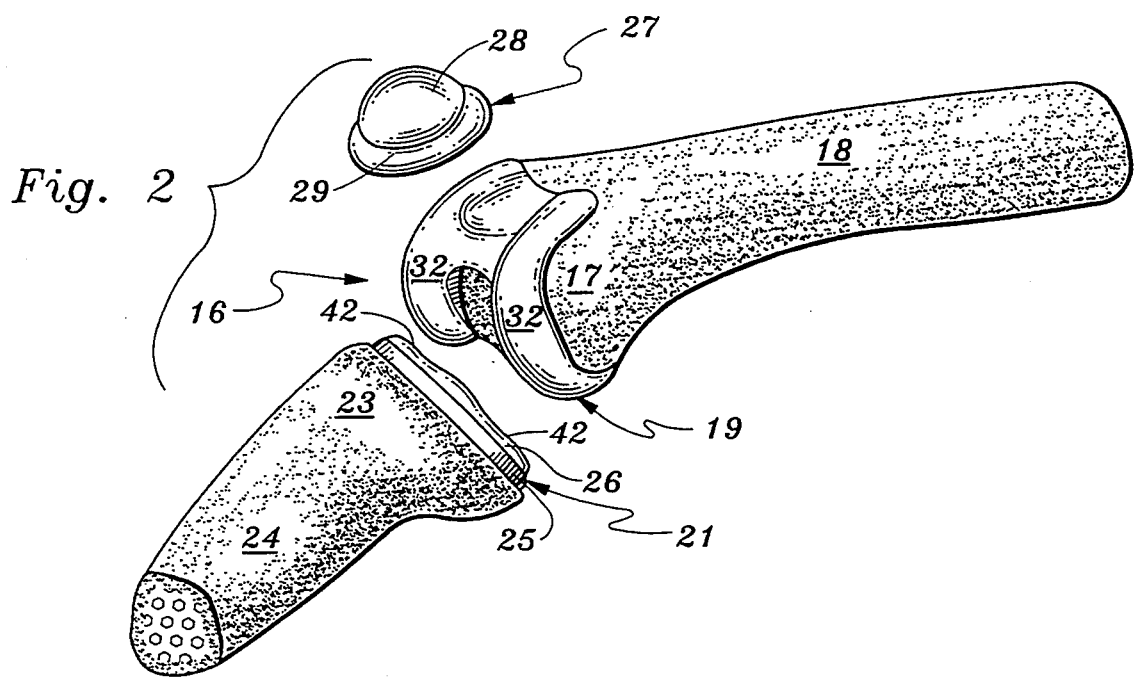
FIG. 2 is a fragmentary, exploded view comparable to FIG. 1 but with the total knee replacement (TKR) prostheses in place, including the femoral component, the patellar component and the tibial component.

As appears most clearly in stylized form in FIG. 2, a total-knee replacement, performed in accordance with any one of several surgical techniques and utilizing any one of a number of femoral, patellar and tibial components, depending upon the system chosen, substantially conforms to the natural knee joint shown in FIG. 1, the components being designed to reproduce the anatomic movement of the knee.

In the total knee replacement (TKR) shown in FIG. 2 and generally designated by the reference numeral 16, the distal end 17 of the femur 18 is provided with a metal cap known as a femoral component 19.

The femoral component 19 is preferably fabricated of metal, such as a cobalt-chromium-molybdenum alloy, and is shaped so that externally it provides substantially the same configuration as the two natural condyles 20 of the femur 18 shown in FIG. 1.

The tibial component 21 of the TKR replaces the cartilaginous meniscus 22 (see FIG. 1) located at the proximal end 23, or head, of the tibia 24 and comprises, in many total knee replacement systems, a composite structure including a fixation plate 25 (see FIG. 2) constructed of a metal alloy, such as the Co—Cr—Mo alloy referred to above, and an articular surface plate 26 of a plastic material, such as ultra-high molecular weight polyethylene.

The patellar component 27 often comprises a composite structure, again of metallic alloy for backing 28 and an articular surface plate 29 of durable plastic material. The patellar component 27 is formed in the button shape of the natural patella 30 (see FIG. 1).

It should be noted that TKR components are available in somewhat different configurations. The implants in any specific case therefore depend upon the particular total knee replacement system chosen by the surgeon. So also, the surgical techniques and manner of use of the various instruments, such as specialized jigs and alignment guides, used in establishing the desired prosthetic fixation and lower limb alignment, will differ somewhat; but are well known and therefore need neither be shown nor described in detail.

As previously indicated, even though the femoral component 19 of a total knee replacement (TKR) is well-fixed and well-aligned, problems can arise if the bearing surfaces of the artificial condyle portions 32 of the femoral component 19 become scratched and abraded as a result of long use of the knee joint. Such abrasions commonly result from the wearing through of the metal backed patellar component 27.

Wearing through of the plastic articular surface plate 26 of the tibial component 21 with resultant metal to metal contact between the fixation plate 25 of the tibial component 21 and the artificial condyles 32 of the femoral component 19, is also a source of problems resulting from abraded metal surfaces.

In either case, revision of one or more total knee replacement (TKR) components has heretofore often been deemed necessary. With the advent of the present procedure, however, the surgeon is provided with an option, depending upon the condition of the entire implant, as revealed by surgical exposure.

Following routine surgical exposure the TKR components are carefully examined. If the surgeon determines, for example, that the components are well-fixed and well-aligned, and that the contours of the bearing surfaces would not be unduly modified by the smoothing process, the present techniques may be elected.

In such case, the abraded portions 31 of the artificial condyles 32, for example, which are the surfaces most commonly affected, would be isolated from the rest of the surgical field. For best results, a secondary dam 33, of transparent plastic material is first installed on the leg as shown in FIG. 6. The secondary dam 33 includes a pair of openings 34 each provided with a perimetral band 35 of elasticized material for a snug fit around the patient's calf and thigh, as shown in FIG. 6. The secondary dam 33 supplements and underlies a primary dam 36 comprising a sheet 37 of transparent plastic material, such as polyethylene, approximately eighteen by twenty-four inches in size.

Figure 4:
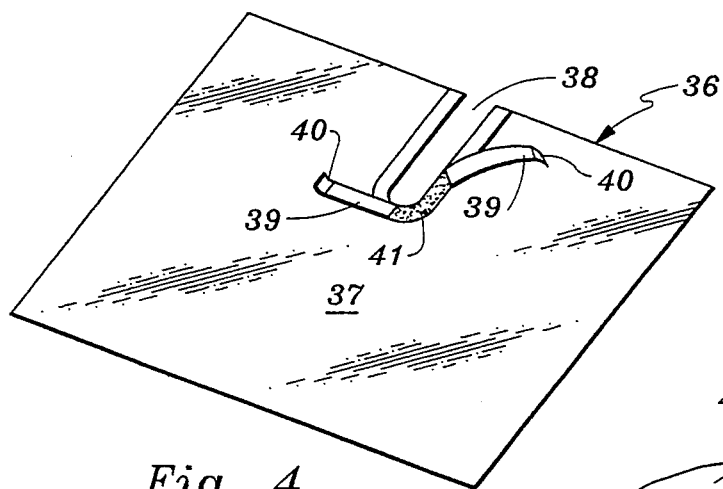
FIG. 4 is a bottom plan view, to a reduced scale, of the primary dam sheet, showing a protective strip partially removed to disclose the underlying pressure sensitive adhesive band.

A slit 38 is formed in the plastic sheet 37 perpendicular to the center of one of the twenty-four inch sides and, as shown most clearly in FIG. 4, a pair of removable protective strips 39 extends the length of the slit 38 along each side and around the bottom thereof. When the primary dam 36 is to be put in place, the strips 39 are removed by pulling on both of the tabs 40, thereby exposing an underlying pressure sensitive adhesive band 41 on each side and around the bottom of the slit 38.

Figure 5:
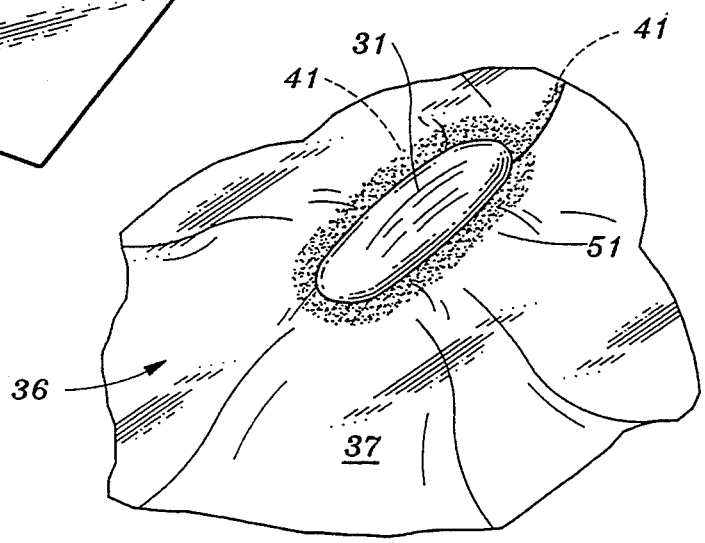
FIG. 5 is a fragmentary perspective view, generally comparable to FIG. 3, but to an enlarged scale, and showing a typical arrangement of a primary drape, or dam, for the isolation of an abraded surface of a femoral component and the interception of debris generated in the course of the surface restoration procedure.

The primary dam 36 is then installed by turning the sheet 37 adhesive side down and placing the object to be polished such as one of the artificial condyles 32, at the base of the slit 38, with the abraded portion 31 to be polished at any one time, protruding upwardly. The adhesive band 41 is then tightly bunched together around the base of the protruding portion into a tightly sealed neck 51, as best appears in FIG. 5.

The steps of smoothing the abraded portion 31 can then be commenced, preferably after first flushing the exposed surface of the artificial condyle 32 with a lavage comprising a conventional saline solution or surgical soap.

In the example disclosed herein, the protruding surface portion to be smoothed constitutes the abraded portion 31 of only one of the artificial condyles 32 of the previously implanted femoral component 19. The other one of the artificial condyles 32 is subsequently smoothed, using a new primary dam 36.

Before proceeding with details of the metal polishing finishing techniques it is believed that a description of the subject matter illustrated in FIG. 3, will enhance an understanding of the present procedure.

In FIG. 3, neither the primary dam 36 nor the secondary dam 33 is shown, in the interests of clarifying the disclosure.

FIG. 3 is particularly intended to illustrate, after surgical exposure, the TKR components, namely, the metallic femoral component 19 with the twin artificial condyles 32 and conforming twin grooves 42 in the plastic articular surface plate 26 forming, along with metallic fixation plate 25, the tibial component 21. Also see FIG. 2.

The everted patellar component 27 shown in FIG. 3 includes the plastic articular surface plate 29 with a substantially centrally located worn-through area 45 revealing the metal backing 28. It is this worn-through area 45 of exposed metal in the patellar component 27 which is responsible for the scratches and abrasions in the affected surface portions 31 of the two artificial condyles 32 of the femoral component 19.

After evaluating the TKR components revealed by the surgical exposure, as in FIG. 3, including the areal extent, location and depth of wear, whether the component is well-fixed and well-aligned, and the desirability in the particular patient of avoiding the damage that revision surgery might have on femoral bone stock, the surgeon might elect to continue the present procedure.

The preferred technique is to remove the scratches and abrasions on the affected surface 31 of the affected artificial condyles 32 in two steps.

First, as best appears in FIG. 3 a high speed, flexible, abrasive rubber wheel 44, mounted, for example, on the spindle of a conventional medical handpiece 46 is manipulated by the gloved hand 47 of the surgeon. In this step, the deep scratches are carefully removed by deft light touches of the wheel 44 to the affected areas.

The rubber, or other flexible material, forming the wheel 44 derives its abrasive qualities from fine grains of an abrasive media, such as diamond or aluminum oxide, embedded in the rubber at the time of manufacture. The abrasive wheel 44 shown in FIG. 3 is but one of several different shapes available, including cylindrical, conical, oval and ball.

Pursuant to the present technique, after the deep scratches and abrasions have been removed to the surgeon's satisfaction by application of the abrasive wheel 44 to the affected portions 31 of the femoral component 19, the affected portions 31 are finish polished by felt bobs 48.

As will be appreciated, the step of flushing accumulated debris at appropriate intervals, with a lavage of saline solution, surgical soaps or the like, forms a part of the polishing procedure. The wash material and debris from the polishing steps are prevented from entering the protected portion of the surgical field by the primary dam 36 and the secondary dam 33, the wash liquid and entrained particles accumulating in a fluid collection pouch 43 at the lower extremity of the secondary dam 33 (see FIG. 6).

Finishing of the previously smoothed portions of the femoral component 19 is preferably effected by a finish polishing bob 48, of felt material, mounted on the spindle of a medical handpiece 46, as before.

The felt type bob 48, or buffing wheel of the desired shape and density are available either in previously impregnated form or it can be impregnated with a sterile buffing compound 49 contained within a sterile disposable cup 50. The buffing compound 49 is in solid state; but, by urging the bob 48 downwardly against the buffing compound 49 while the bob is rotating, as shown in FIG. 7, the solid state compound in the vicinity of the bob is melted by frictional heat, allowing the liquefied sterile compound 49 to adhere to and impregnate the felt material of the bob 48.

The medical handpiece 46 is then manipulated so that the impregnated felt buffing wheel 48 is brought to bear against the previously smoothed portions of the femoral component 19 with a specific orientation, as appears in FIG. 8.

In the interests of clarity, the primary dam 36 and the secondary dam 33 illustrated in FIG. 6 are shown removed in FIG. 8. The felt bob 48 shown in FIG. 8 (as well as in FIG. 7) is of right circular cylindrical configuration. With the cylindrical bob 48 oriented as appears in FIG. 8, the peripheral surface of the bob 48 is gently used to blend and feather edge the previously smooth-polished areas. As in the case of the previously described rubber bonded abrasive wheels 44, the felt bobs are available in a variety of shapes and sizes to suit the particular surface or contour to be polished.

In order to modify the contour of the surface of the previously polished portions to a minute degree, should such contouring seem necessary, the effective velocity of the buffing surface of the bob can be reduced by selecting an oval-shaped felt bob 52 and positioning the handpiece 46 so that the bob 52 is oriented as appears in FIG. 9.

At the conclusion of the finish polish step, the surface roughness is frequently reduced to a degree comparable with that of a new TKR femoral component 19. The condyles 32 present a highly reflective and, in all cases, a substantially mirror-like finish.

As noted above, FIGS. 3, 8 and 9 omit both the primary dam 36 and the secondary surgical drape 33, in the interests of clarity. In the preferred method, however, the primary dam 36 is utilized, in the arrangement shown to an enlarged scale in FIG. 5, with the portion 31 to be smoothed, at any one time, protruding upwardly from the tightly bunched up and adhesively sealed neck 51 of the primary dam 36.

After one of the artificial condyles is smoothed and polished to a "like new" condition, to the surgeon's satisfaction, the primary dam 36 is removed and discarded. A new primary dam 36 is then readied by removing the protective strips 39, turning over the sheet 37 and installing the dam 36 on the second condyle 32. The primary polishing step and the secondary, or finish, polishing step are then repeated on the second condyle, including feather edging and surface contouring if deemed necessary.

After polishing and finishing have smoothed the entire affected portions of the femoral component 19 to the extent desired by the surgeon, the patellar component 27 is replaced, as well as the tibial component 21. This is followed by routine surgical procedure to complete the arthroplasty.

What is claimed is:

1. Method of restoring the surface smoothness of an abraded femoral component of a total knee replacement including a femoral component and a patellar component comprising:
   a. surgically exposing the abraded portions of the femoral and patellar components;
   b. observing the surface smoothness of the abraded portion of the femoral component;
   c. isolating the abraded portion of the femoral component with a dam;
   d. polishing the abraded portion of the femoral component by the application of an abrasive wheel to said portion until the abrasions are substantially eliminated;
   e. finish polishing the smoothed surface by the application of a felt bob impregnated with polishing compound; and,
   f. surgically completing the arthroplasty.

2. Method as in claim 1 further including step d(1). between steps d. and e. of intercepting in the dam any debris generated by step d.

3. Method as in claim 2 including step e(1). between steps e. and f. of intercepting in the dam any debris generated by step e.

4. Intraoperative method of restoring the surface smoothness of total knee replacement components comprising:
   a. surgically exposing the components;
   b. comparing the roughness of the abraded surfaces of the replacement components with the comparable surfaces of new components;
   c. polishing the abraded surfaces with an abrasive wheel;
   d. comparing the polished surfaces with new surfaces;
   e. buffing the polished surfaces until new surface smoothness is substantially attained; and,
   f. surgically completing the arthroplasty.

5. Method as in claim 4 further including step b(1) between steps b. and c. of isolating the abraded surfaces from the surgical field with a dam.

6. Intraoperative method of restoring the surface smoothness of arthroplastic implants comprising:
   a. surgically exposing the implants;
   b. comparing the roughness of the abraded surfaces of the implants with the comparable surfaces of new implants;
   c. smoothing the abraded surfaces until new surface smoothness is substantially attained; and,
   d. surgically completing the arthroplasty.

7. Method as in claim 6 further including step a(1) between steps a. and b. of isolating the surgical field from the abraded surfaces to be smoothed.

* * * * *